United States Patent [19]

Zander et al.

[11] Patent Number: 5,596,983
[45] Date of Patent: Jan. 28, 1997

[54] APPARATUS FOR OXYGENATING A PATIENT

[76] Inventors: Rolf Zander, Luisenstrasse 17, DE-6500 Mainz; Friedrich Mertzlufft, Katzenberg 31, 6500 Mainz 21 DE, both of Germany

[21] Appl. No.: 957,740

[22] Filed: Oct. 7, 1992

Related U.S. Application Data

[63] Continuation-in-part of Ser. No. 672,184, Mar. 20, 1991, abandoned.

[30] Foreign Application Priority Data

Mar. 15, 1991 [DE] Germany ................... 40 09 008.6

[51] Int. Cl.⁶ .................................................. A61M 16/00
[52] U.S. Cl. ........................ 128/204.18; 128/207.12; 128/207.13
[58] Field of Search ................ 128/205.13, 205.17, 128/207.13, 205.23, 204.18, 207.12

[56] References Cited

U.S. PATENT DOCUMENTS 1,362,766  12/1920  McGargill .
1,443,820   1/1923  Hudson .
2,432,627  12/1947  Margaria ........................... 128/205.17
4,350,647   9/1982  de la Cruz ......................... 128/205.23

FOREIGN PATENT DOCUMENTS 27599  1/1904  United Kingdom ............. 128/207.13

Primary Examiner—Aaron J. Lewis
Attorney, Agent, or Firm—Michael L. Dunn

[57] ABSTRACT

An apparatus is provided for oxygenating a patient, comprising an oxygen supply means with an oxygen applicator for supplying oxygen via the nose, the oxygen applicator being a closed system, with the applicator affixable about the nose in a tightly-sealable manner so that it supplies pure oxygen solely via the nose in a directed flow, and additionally comprising a one-way valve which can be inserted in substantially sealing-tight manner into the mouth of the patient, the one-way valve opening only upon gas outflow out of the mouth, the closed system at all times having a pressure which is greater than the pressure necessary to open the one-way valve, such that respired air from the patient can escape only through the mouth and no air can escape through the nose.

14 Claims, 2 Drawing Sheets

APPARATUS FOR OXYGENATING A PATIENT

This is a Continuation-in-part of application Ser. No. 07/672,184, filed Mar. 20, 1991 now abandoned.

BACKGROUND OF THE INVENTION

Warm blood cells rely on a continuous and adequate demand-orientated supply of oxygen so that even a brief interruption in the supply of oxygen can cause irreparable damage in and on the cells, particularly of the central nervous system and the cardiac circulatory system.

A shortage of oxygen, hypoxia, can be caused principally by inadequate supply, disorders of the pulmonary function, disorders in the conveyance of oxygen through the blood or a lack of hemoglobin and also by disorders in the cardiac circulatory system. In emergency medicine as well as in internal clinical supply, therefore, it is standard practice to supply oxygen to a patient. Within the framework of what is referred to as preoxygenation, above all before any intubation, it is vitally necessary to cover the patient's oxygen demand in the dangerous period prior to completion of the intubation or in the event of intubation complications.

In such and other cases, it is vital to enrich the storage space in the lungs with pure oxygen and at the same time also to ensure that other gases present in the body or in the inspired air, above all nitrogen, are as far as possible kept completely away. In most cases, this is either not achieved at all or is achieved only very inadequately by conventional pre-oxygenation methods. Known oxygenation apparatuses are masks, pharyngeal tubes and nasal-pharyngeal tubes, referred to as just tubes.

The disadvantages of these apparatus, described in the literature (e.g. R. G. Sandersen [ed.]: The Cardiac Patient, Philadelphia, W. B. Saunders, 1972, page 310), are above all insufficient humidification and warming of the gas, oxygen concentration is never 100%, re-inhalation of respired air ($CO_2$ and $N_2$) and a very high oxygen flow.

The problem on which the invention is based therefore resides in providing an apparatus for supplying oxygen to a patient (oxygenation), by means of which, simultaneously with the enrichment of oxygen, undesired other gases are as far as possible kept completely out of the pulmonary space.

In addition, it is intended to eliminate the above-mentioned drawbacks of prior art apparatus.

SUMMARY OF THE INVENTION

Figure 1:
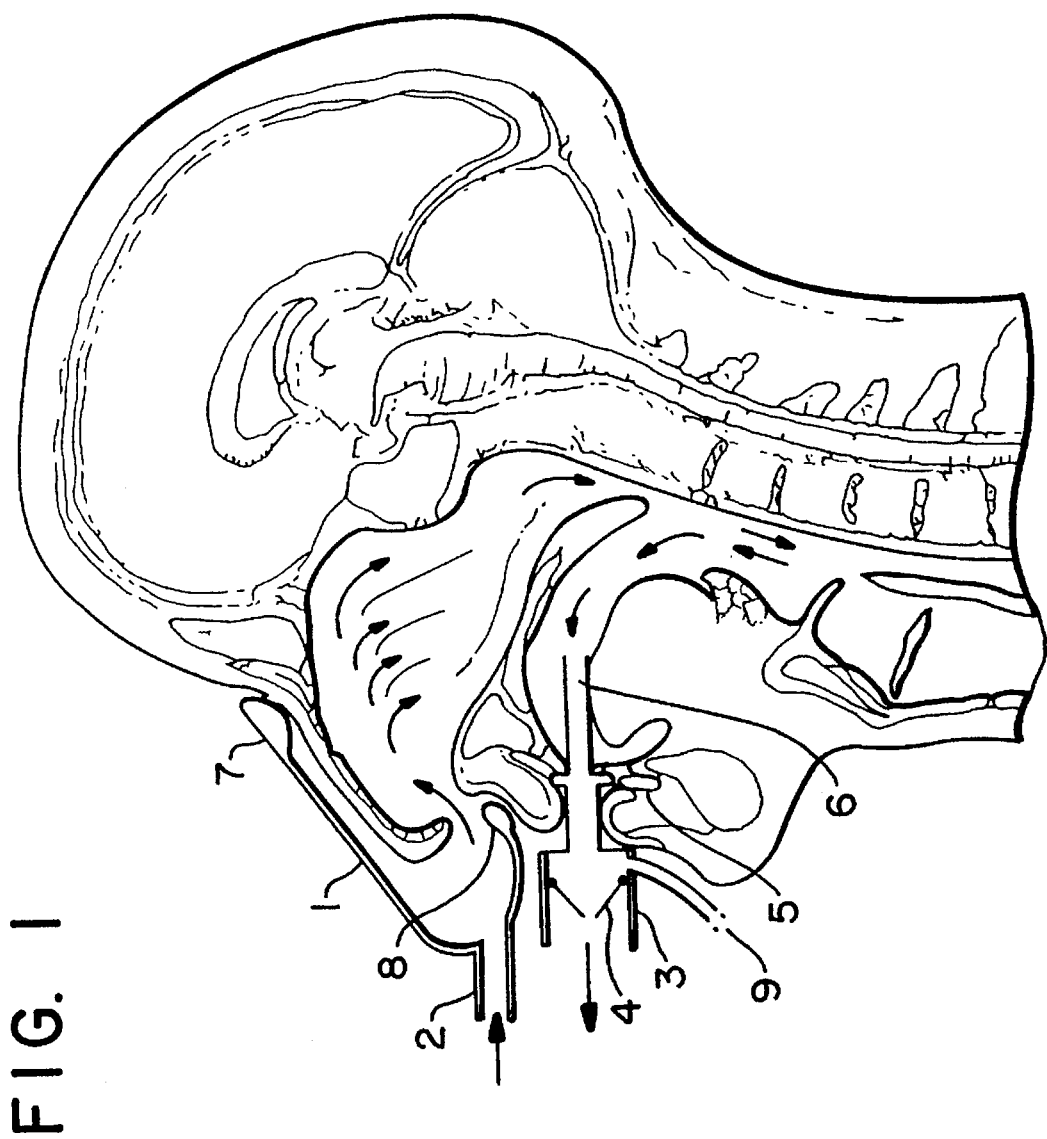
FIG. 1 shows a side cross-sectional view of an apparatus according to the invention showing application 1 in the form of a mask with two sealing lips 7 and 8 applied above and below the nose.

According to the invention, this apparatus of oxygenating a patient is provided with an oxygen applicator for supplying oxygen via the nose and is characterized in that the oxygen applicator is constructed and affixed in a tightly-sealable manner with respect to the nose so that it supplies pure oxygen solely via the nose (nasal) in a directed flow (nasoral) and in that the apparatus additionally comprises a one-way valve adapted to be inserted at least substantially in sealing-tight fashion into the mouth (oral) of the patient and which opens only during gas outflow. The oxygen applicator is a closed system, which is sealingly affixed to the patient's face, with no venting to the atmosphere, and is therefore at all times under a pressure which prevents respired air to leave or escape via the nose. This is because the pressure within the applicator system, which varies depending upon whether or not oxygen is being applied, is always greater than the pressure required to open the one-way valve in the mouth. Since the respired air naturally follows the path of least resistance to flow, all of the respired air necessarily escapes through the mouth, and no air escapes through the nose.

In one aspect, the invention refers to an apparatus for oxygenating a patient, comprising an oxygen supply means with an oxygen applicator for supplying oxygen via the nose, the oxygen applicator being a closed system constructed in a tightly-sealable manner concerning the nose so that it supplies pure oxygen solely via the nose in a directed flow, and additionally comprising a second one-way valve which can be inserted in substantially sealing-tight manner into the mouth of the patient, said second one-way valve opening only upon gas overflow out of the mouth, otherwise closing and allowing excess oxygen and expired air to escape solely through the mouth.

In principle, it is possible with this apparatus to ensure on the one hand:

a directed flow, namely a separation of inhalation (100% $O_2$ via the nose) and exhalation (excess $O_2$, $N_2$ and $CO_2$ via the oral valve), i.e. a "nasoral" system is achieved, and a physiological flow, namely humidification and heating, is retained via the nose without increasing the dead space and avoiding any re-inhalation.

DETAILED DESCRIPTION OF THE INVENTION

This apparatus ensures that if breathing is present or in the process of ceasing (apnoea) only pure (warmed and humidified) oxygen can reach the patient's respiratory passages and lungs, all gases which should be eliminated (nitrogen, laughing gas, carbon dioxide) are completely ($N_2$, $N_2O$) or physiologically ($CO_2$ discharged through the oral valve.

Even if the patient is unable to breathe independently, this apparatus is capable of allowing the patient to "inhale" only pure oxygen (referred to as apnoic oxygenation), since the one-way valve prevents the uncontrolled and undesired penetration of ambient air and thus large quantities of nitrogen. This functions for an unlimited period. As soon as respiration ceases, intentionally (for untubation) or unintentionally (an emergency), the oral valve can be removed if it is ensured that excess oxygen escapes through the mouth. In this situation, therapeutic measures can be undertaken via the mouth (e.g. vacuum extraction, intubation, haemostasis), but also diagnostic measures are possible (e.g. bronchoscopy, laryngoscopy). The doctor, nurse or auxiliary also have both hands free for any necessary routine or acutely desired measure such as for example in an emergency the setting up of instruments for artificial respiration and the corresponding drugs or also the provision of a peripherovenous access for the administration of life saving or also anesthesiologically vital medicaments or blood or blood substitutes. Also, the doctor, lay helper or auxiliary will have both hands free for resuscitation measures such as for example extrathoracic cardiac massage, defibrillate, injections or infusions. A further advantage of the apparatus resides in the fact that it even allows a lay person significantly and without risk to increase the existing supply of oxygen which is minimal under normal conditions, which is of great benefit over the entire range of extraclinical and intraclinical patient care for daily routine work. Assistance on the part of the patient is unnecessary. Thus, the apparatus can be advantageously used in cases of hypoxia of varying origin or for pre-oxygenation prior to intubation. With these cases, the apparatus according to the invention will prior reduce the overall risk which exists especially by reason of possible obstacles to intubation.

The same apparatus can be used universally, namely both in emergency medicine (patient conscious or unconscious, breathing present or faltering) and also in anesthesiology (pre-operative: pre-oxygenation, post-operative: recovery room), in intensive care (weaning of respirator), in otorhinolaryngology (laryngoscopy), in pulmology (bronchoscopy) and in dental, oral and maxillary treatment (oral surgery).

An essential feature of the apparatus according to the invention is that the introduction of the oxygen takes place solely via the nose. Oxygen overflow and exhalation pass through the mouth which is prevented from drawing in air by the one-way valve.

Preferably, the apparatus comprises additionally a one-way valve inserted in substantially sealing-tight manner into the oxygen supply means, the one-way valve opening only upon gas inflow, otherwise closing. Suitably, between the oxygen source and the oxygen applicator an oxygen bag is interposed.

The oxygen applicator can be constructed in various ways and its supply part can for example take the form of a nasal catheter. Expediently, however, an oxygen applicator in the form of a mask will be used, the mask covering only the nose. This mask is so constructed that it can be placed over the nose in a substantially sealing-tight manner.

In per se known manner, the oxygen applicator can be connected to an oxygen bag interposed between the oxygen source and the oxygen applicator, allowing the inhalation process to be observed. In addition to or instead of the oxygen bag, an acoustic or visual signal may be provided on the oxygen applicator and/or on the one-way valve, to be triggered when the desired inhalation or exhalation takes place or when gas is flowing in or out.

In order to guarantee a unique (inner-hospital and pre-hospital) application of the oxygen bag the setting as described below should be followed: The oxygen bag connected to the oxygen tube 2 of the oxygen applicator 1 comprises 22 mm $\phi$ connection (DIN-ISO 5356 part I) allowing for direct connection to both the oxygen applicator 1 as well as to any endotracheal intubation tubes, the comprised 6 and 15 mm $\phi$ connecting combination additionally allows for both direct connection to the central oxygen supply via the installed ventilation system (15 mm $\phi$, DIN-ISO 7228) and, via the integrated 6 mm connector (ISO 594/1) to mobile oxygen supply sources (e.g. oxygen cylinders).

After performance of endotracheal intubation (one-way valve 3 removed), clamped-sealing and disconnection of the oxygen bag from the oxygen tube 2, the described setting provides the possibility to maintain oxygenation/denitrogenation (mobile oxygenation, e.g. for transport of patients from the induction room to the operation theatre and from operation theatre to the recovery room or intensive care unit, for any measure of patient positioning).

As stated above, the one-way valve is so constructed that it can be inserted in substantially sealing-tight manner into the patient's mouth. For this purpose, the one-way valve is expediently provided with a flexible sealing plate which is introduced into the patient's mouth in front of the top and bottom jaws and between them and the lips. It is especially expedient if there is adjacent to this sealing plate a tubular member which projects into the pharyngeal space and on which the patient is able to bite in order to maintain the sealing plate in a sealing-tight position.

However, it is of course also possible for the one-way valve to be sealed in other ways such as for example by a possibly inflatable rubber balloon which fits tightly in the mouth opening during inflation.

The two devices which form part of the apparatus according to the invention, the oxygen applicator and the one-way valve, can be provided separately from each other, as a set. However, it is expedient for them to be connected to each other so that the user, the doctor, the nurse or the auxiliary, always has both devices available together, ready for use.

Figure 2:
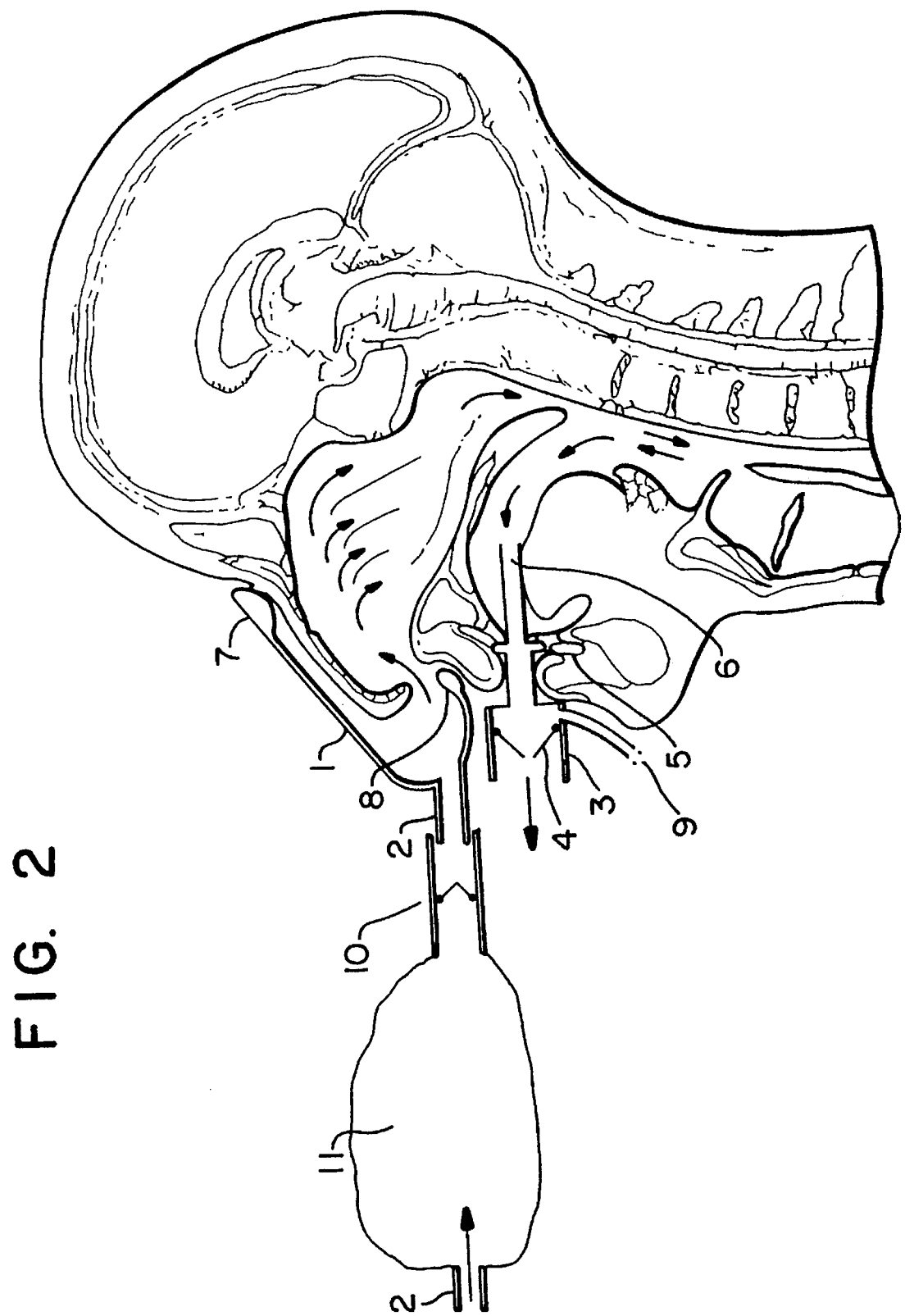
FIG. 2 shows a side cross-sectional view of an embodiment additionally comprising an oxygen bay 11 and a second one-way valve 10.

The accompanying drawing shows in FIG. 1 a first and in FIG. 2 a second embodiment of the apparatus according to the invention diagrammatically and in vertical section.

Referring to FIG. 1 the apparatus according to the invention consists of the oxygen applicator 1 and the one-way valve 3. The oxygen applicator device 1 takes the form of a mask with two sealing lips 7 and 8 which are applied above and below the nose and allow oxygen to be supplied solely via the nose. The oxygen applicator 1 is connected to an oxygen tube 2 which is connected to an oxygen cylinder, possibly via an oxygen bag.

The embodiment according to FIG. 2 comprises additionally an oxygen bag 11 and a second one-way valve 10 both inserted into the oxygen tube 2. This one-way valve opens only upon gas inflow from the oxygen source (not shown).

The one-way valve 3 has a flexible sealing plate 5 which can be inserted in a substantially sealing-tight manner between the lips and jaws (teeth) of the patient. Adjacent to this sealing plate 5 is a tubular member 6 on which the patient bites. In the widened out front part of the one-way valve which is outside the mouth, there are the valve members 4 which are so constructed that they spread apart from one another during exhalation or during gas outflow, whereas they otherwise are pressed in sealing-tight manner on one another (for example during the inhalation process) and prevent the ingress of ambient air.

Under clinical conditions, the denitrogenation as well as the ventilation of the patient can be controlled by endexpiratory gas sampling using either mass spectrometry ($O_2$, $CO_2$, $N_2$) or capnometry ($O_2$, $CO_2$): For this occasion the one-way valve 3 comprises a special and closable gas outlet 9 allowing for the connection of the respective analyzing system (ISO 594/1) and thus for continuous gas sampling (side stream).

What is claimed is:

1. An apparatus for oxygenating a patient, comprising an oxygen supply means with an oxygen applicator for supplying oxygen via the nose, the oxygen applicator being a closed system, said applicator affixable about the nose in a tightly-sealable manner so that it supplies pure oxygen solely via the nose in a directed flow, and additionally comprising a one-way valve which can be inserted in substantially sealing tight manner into the mouth of the patient, the one-way valve opening only upon gas outflow out of the mouth, said closed system at all times having a pressure which is greater than the pressure necessary to open said one-way valve during gas outflow, such that respired air from the patient can escape only through the mouth and no air can escape through the nose.

2. An apparatus according to claim 1, comprising an oxygen bag interposed between the oxygen source and the oxygen applicator.

3. An apparatus according to claim 1, wherein the oxygen applicator is constructed as a mask which only is connected to the nose.

4. An apparatus according to claim 1, wherein the one-way valve which can be inserted into the mouth comprises a flexible sealing plate adapted to be introduced between the lips and the jaws or teeth of the patient.

5. An apparatus according to claim 4, wherein the one-way valve comprises a tube portion adjacent the sealing plate.

6. An apparatus according to claim 1, wherein the one-way valve comprises flexible plates which are spread apart from one another only upon gas outflow being otherwise pressed against one another in substantially sealing-tight manner.

7. An apparatus according to claim 1, wherein the oxygen applicator and the one-way valve are connected to each other.

8. An apparatus according to claim 1, wherein the one-way valve which can be inserted into the mouth generates a visual or acoustic signal for the period during which it is open.

9. An apparatus according to claim 1, wherein the one-way valve which can be inserted into the mouth generates a visual or acoustic signal upon being opened and closed.

10. An apparatus according to claim 1, wherein the one-way valve contains a closable gas outlet having a 6 mm diameter allowing continuous endexpiratory gas sampling for gas analysis.

11. An apparatus according to claim 1, wherein the oxygen tube of the oxygen applicator comprises a connection with a 2 mm diameter.

12. An apparatus according to claim 1, wherein the oxygen tube of the oxygen applicator comprises a combined connection of 6 and 15 mm diameters, the 6 mm connector being part of a 15 mm connector.

13. An apparatus for oxygenating a patient, comprising an oxygen supply means with an oxygen applicator for supplying oxygen via the nose, a first one-way valve inserted in a substantially sealing-tight manner into the oxygen supply means, said first one-way valve opening only upon gas inflow into the nose, otherwise closing, said oxygen applicator being constructed in a tightly-sealable manner concerning the nose so that it supplies pure oxygen solely via the nose in a directed flow, and additionally comprising a second one-way valve which can be inserted in substantially sealing-tight manner into the mouth of the patient, said second one-way valve opening only upon gas outflow out of the mouth, otherwise closing, and allowing excess oxygen and expired air to escape solely through the mouth; wherein the one-way valve which can be inserted into the mouth generates a visual or acoustic signal for the period during which it is open.

14. An apparatus for oxygenating a patient, comprising an oxygen supply means with an oxygen applicator for supplying oxygen via the nose, a first one-way valve inserted in a substantially sealing-tight manner into the oxygen supply means, said first one-way valve opening only upon gas inflow into the nose, otherwise closing, said oxygen applicator being constructed in a tightly-sealable manner concerning the nose so that it supplies pure oxygen solely via the nose in a directed flow, and additionally comprising a second one-way valve which can be inserted in substantially sealing-tight manner into the mouth of the patient, said second one-way valve opening only upon gas outflow out of the mouth, otherwise closing, and allowing excess oxygen and expired air to escape solely through the mouth; wherein the one-way valve which can be inserted into the mouth generates a visual or acoustic signal upon being opened and closed.

* * * * *